United States Patent [19]
Sonobe et al.

[11] Patent Number: 4,758,437
[45] Date of Patent: Jul. 19, 1988

[54] COMPOSITION FOR LONG ACTING NICARDIPINE PREPARATION AND PROCESS OF PRODUCING THE COMPOSITION

[75] Inventors: Takashi Sonobe; Hiroitsu Kawata; Masayoshi Aruga, all of Saitama; Tadayoshi Ohmura, Shizuoka; Satoru Yoneya, Saitama; Chiharu Yamada, Saitama; Yukio Kubota, Saitama, all of Japan

[73] Assignee: Yamanouchi Pharmaceutical Co., Ltd., Tokyo, Japan

[21] Appl. No.: 13,326

[22] Filed: Feb. 11, 1987

Related U.S. Application Data

[63] Continuation-in-part of Ser. No. 520,345, Aug. 4, 1983, abandoned.

[51] Int. Cl.$^4$ .......................... A61K 9/14; A61K 9/16; A61K 9/20; A61K 31/74
[52] U.S. Cl. ................................ 424/471; 424/457; 424/501; 424/502
[58] Field of Search ................ 424/471, 457, 501, 502

[56] References Cited

U.S. PATENT DOCUMENTS

| | | | |
|---|---|---|---|
| 3,954,959 | 5/1976 | Pederson | 424/32 X |
| 4,193,985 | 3/1980 | Bechgaard et al. | 424/32 X |
| 4,223,006 | 9/1980 | Taskis | 424/33 X |
| 4,261,971 | 4/1981 | Appelgren et al. | 424/32 X |
| 4,343,789 | 8/1982 | Kawata et al. | 424/32 X |
| 4,353,888 | 10/1982 | Sefton | 424/32 X |

FOREIGN PATENT DOCUMENTS

2397840  3/1979  France .................................. 424/32

*Primary Examiner*—Michael R. Lusignan
*Attorney, Agent, or Firm*—Burgess, Ryan & Wayne

[57] ABSTRACT

A spherical pellet like composition of nicardipine composed of small granular nuclei such as sugar particles coated with amorphous nicardipine or a salt thereof, a pH-dependent additive and a surface active agent. The spherical pellet like composition of nicardipine may have a further coating of a medicament permeating material as an outermost coating. The spherical pellet like composition may be mixed with the spherical pellet like composition coated with the medicament permeating material.

13 Claims, No Drawings

COMPOSITION FOR LONG ACTING NICARDIPINE PREPARATION AND PROCESS OF PRODUCING THE COMPOSITION

This application is a continuation-in-part of Ser. No. 06/520,345 filed 8/4/83, now abandoned.

FIELD OF THE INVENTION

This invention relates to a composition for a long acting or long lasting preparation of nicardipine (chemical name: 2,6-dimethyl-4-(3'-nitrophenyl)-1,4-dihydropyridine-3,5-dicarboxylic acid-3-methyl ester-5-$\beta$-(N-benzyl-N-methylamino)-ethyl ester) or a salt thereof and also to a process of producing the composition.

BACKGROUND OF THE INVENTION

Nicardipine possesses a coronary dilator activity and a cerebral vascular dilator activity, and is a medicament useful for curing cerebral vascular disease, hypertension, and angina pectoris. Since nicardipine or its salt has a good solubility in the first fluid of Japanese Pharmacopeia IX (a fluid of about pH 1.2 prepared by adding 24.0 ml of diluted hydrochloric acid and water to 2.0 g of sodium chloride to make 1,000 ml of the solution), it exhibits sufficiently the medical activity in usual preparations but since nicardipine is sparingly soluble in the second fluid of Japanese Pharmacopeia IX (a fluid of about pH 7.5 prepared by adding 6.0 ml of diluted hydrochloric acid and water to 35.8 g of disodium hydrogenphosphate to make 1,000 ml of the solution) and is practically insoluble in intestinal juice, it is difficult to prepare an effective, long acting preparation of nicardipine.

Since a long acting preparation has many therapeutic advantages such as the reduction in dosing frequency of the medicament, long acting effective concentration of medicament in blood, etc., various general long acting preparations have hitherto been developed. For example, there are preparations having compounded therewith a large amount of a material which does not disintegrate in the stomach or intestines, a preparation formed by coating pellets or tablets with a water repellent, and also a preparation formed by mixing a medicament with a sparingly soluble or hydrophilic high molecular compound or by adsorbing the high molecular compound onto a medicament, whereby the medicament is gradually released. However, in the case of a medicament having a low solubility in an intestinal juice such as nicardipine or a salt thereof, a long acting effect cannot be obtained by such conventional long acting preparations. That is, the application of the foregoing conventional long acting technique to such a medicament may cause only the reduction of bioavailability and hence, in the case of such a medicament, it is necessary to compound therewith an additive for improving the solubility thereof in an intestinal juice to improve the solubility of the medicament.

Therefore, various processes of producing long acting preparations of nicardipine have been proposed. For example, there is a process of producing a long acting preparation of nicardipine by dissolving nicardipine in water or organic solvent(s) together with (a) hydroxypropylmethyl cellulose (HPMC), hydroxypropyl cellulose (HPC), methyl cellulose (MC), etc., and further, it desired, (b) polyethylene glycol, a surface active agent, etc., removing water or the organic solvent to form solid material, pulverizing, if necessary, the solid material, and then adding thereto polyethylene oxide (PEO); or by adding PEO to nicardipine and the components (a) and (b), dissolving the mixture in water or organic solvents(s), removing the water or the organic solvent(s) to form a solid material, pulverizing, if necessary, the solid material, and then forming the preparation using the solid material or the pulverized solid material (Japanese Patent Application (OPI) No. 49,314/'81) and a process of producing a long acting preparation of nicardipine by, if necessary friction-pulverizing nicardipine crystals and adding a pH-dependent additive, diluents, etc., to the nicardipine crystals before or after pulverizing them (Japanese Patent Application (OPI) No. 133,217/'81). However, the preparations obtained by these processes are objectionable in that the concentration of the medicament does not reach an effective plasma level in a short period of time after the administration i.e., the clinically effective plasma level is not sufficiently maintained, the intersubject variation of plasma of concentration is large, etc.

SUMMARY OF THE INVENTION

Under these circumstances, as the result of various investigations on long acting preparation of nicardipine, the inventors have discovered that a spherical pellet like composition (Composition A) formed by coating small granular nuclei with (a) amorphous nicardipine or a salt thereof, (b) a pH-dependent additive and a surface active agent and a spherical pellet like composition (Composition B) formed by further coating the foregoing composition (Composition A) with a medicament-permeating material provides an excellent long acting effect. Furthermore, it has been discovered that by mixing Composition A and Composition B at an appropriate ratio, a composition having a desired long acting effect is obtained. Based on these discoveries, the invention has been attained.

Thus, the invention provides a spherical pellet like long acting composition comprising small granular nuclei coated with (a) amorphous nicardipine or a salt thereof and (b) a pH-dependent additive.

The foregoing composition may have further been coated with (c) a medicament-permeating material.

By using the composition of this invention, the solubility of nicardipine in an intestinal juice can be remarkably improved, the intersubject variation of plasma concentration can be reduced to a significant extent and the clinically effective plasma level can be maintained for a long period of time as compared to conventional preparation of nicardipine.

DESCRIPTION OF THE PREFERRED EMBODIMENT

Composition A of this invention can be produced by dissolving (a) nicardipine or a salt thereof, (b) a pH-dependent additive and a surface active agent in an organic solvent or a mixture of water and an organic solvent and coating small granular nuclei with the solution by, e.g., spray coating. Also, composition B can be produced by further spray-coating composition A with a solution of a medicament permeating material dissolved in an organic solvent.

More preferably, composition A can be obtained by dissolving (a) nicardipine or a salt thereof, (b) a pH-dependent additive and a surface active agent in an organic solvent such as methanol, ethanol, isopropanol, chloroform, acetone, methylene chloride, etc., a mixture of them, or a mixture of water and the foregoing organic solvent and coating small granular nuclei composed of crystalline cellulose, a mixture of sugar and corn starch, a mixture of crystalline cellulose and lactose etc., (e.g., Nonpareil, trade name, made by Freund Industrial Co., Ltd.) by a spray coating method, such as, a centrifugal fluidized coating method, a fluidized bed coating method, etc. Also, Composition B of this invention can be obtained by further coating the composition A thus obtained with a solution of a medicament permeating material dissolved in the foregoing organic solvent by, for example, a spray coating method to form, thereby, a layer of the medicament permeating material on the composition. In such a production process of the preparation, nicardipine or a salt thereof is converted into the amorphous form.

Examples of the foregoing pH-dependent additives are hydroxypropylmethyl cellulose phthalate, cellulose acetate phthalate, Eudragit-L and -S (trade names, made by Rohm and Haas Co., component: a poly(methacrylic acid, methylmethacrylate), etc. Examples of the surface active agent used in this invention are Tween 80 (trade name, made by Kao Atlas Co., component: polyoxyethylene sorbitan mono-oleate); Renex 30 (trade name, made by ICI Co., component: polyoxyethylene alkyl ether), Nikkol HCO-60 (trade name, made by Nikko Chemicals Co., Ltd., component: polyoxyethylene-hydrogenated castor oil); etc. Furthermore, examples of the medicament permeating material are Eudragit RL and RS (trade names, made by Rohm and Haas Co., component; poly(ethylacrylate, methylmethacrylate, -trimethylammonioethylmethacrylate chloride) Ethocel (trade name, made by Dow Chemical Co., component: ethyl cellulose), and they may be a mixture thereof with water-soluble polymers, e.g. HPC (trade name, made by Shin-Etsu Chemical Co., Ltd., composition: hydroxypropyl cellulose); Macrogol 400, 1500 and 6000 (Jap. Pharmacopeia X, component: polyoxyethylene glycol), Metholose (trade name, made by Shin-Etsu Chemical Co., Ltd., composition: methyl cellulose); TC-5 (trade name, made by Shin-Etsu Chemical Co., Ltd. component: hydroxypropylmethyl cellulose).

In composition A, the ratio of the coating to the small granular nucelus is 1:0.1 to 1:10 and in composition B, the ratio of the medicament permeating material to the composition A is 15:85 to 1:99.

Also, in the mixture of composition A and composition or composition A' (which is obtained by using the foregoing water-soluble polymer or a mixture of pH-dependent additive and the water-soluble polymer in place of the dependent additive: cf. Reference Examples 1 and 2) and composition B, the effective concentration of nicardipine in blood can be maintained for a longer period of time than the case of using each composition solely since there is a difference in the rate of dissolution between both the compositions. Furthermore, if a composition of nicardipine showing a high concentration in blood immediately after administration and also maintaining the concentration for a long time is desired, the object can be attained by using composition A or A' having a low lasting property (or almost no lasting property) and composition B having a long lasting property. Such a composition can be obtained by blending composition A or A' and Composition B at a ratio of 1:0.5 to 1" 19 by a conventional method.

The composition of this invention can be administered as the form of itself or may be filled in a capsule by a conventional method and administered as the capsulated composition.

Compositions of this invention are tested for the long acting effect and the results are shown in Tables 1 and 2.

TABLE 1

Concentration of the drug in blood in case of oral administration to a Beagle dog.

| Sample | No. of dogs | Dose | Concentration in plasma (ng/ml) (± s.e.)[2] | | | | | | | | | | | |
|---|---|---|---|---|---|---|---|---|---|---|---|---|---|---|
| | | | 0 hr | 0.5 hr | 1 hr | 2 hrs | 3 hrs | 4 hrs | 5 hrs | 5.5 hrs | 6 hrs | 7 hrs | 8 hrs | 10 hrs |
| Control[1] | 8 | 40 mg/body twice | 0 (0) | 113.2 (21.7) | 123.9 (24.7) | 53.5 (11.2) | 19.0 (11.2) | | 7.5[3] (1.4) | 43.6 (15.6) | 113.5 (23.9) | 82.8 (16.7) | 34.7 (11.0) | 13.6 (3.0) |
| Composition of Ex. 1 | 5 | 40 mg/body | 0 (0) | | 77.1 (38.6) | 177.6 (31.4) | | 56.0 (17.9) | | | 26.9 (6.3) | | | 10.3 (2.4) |

[1]Conventional powder form preparation
[2]Standard error
[3]Second administration

TABLE 2

Concentration of the drug in blood in case of oral administration to human.

| Sample | No. of humans | Dose | Concentration in plasma (ng/ml) (± s.e.)[2] | | | | | | | | | | | |
|---|---|---|---|---|---|---|---|---|---|---|---|---|---|---|
| | | | 0 hr | 1 hr | 2 hrs | 3 hrs | 4 hrs | 6 hrs | 8 hrs | 10 hrs | 12 hrs | 14 hrs | 16 hrs | 20 hrs | 24 hrs |
| Composition of Ex. 2 | 3 | 40 mg/body | 0 (0) | 6.8 (1.1) | 16.3 (5.5) | 24.9 (8.2) | 74.3 (28.0) | 12.6 (1.8) | 12.7 (4.3) | 4.4 (1.3) | | | | | 1.8 (1.7) |
| Composition of Ex. 5 | 3 | 40 mg/body | 0 (0) | 0.4 (0.4) | 2.7 (1.8) | | 37.0 (18.4) | 27.7 (9.0) | 15.1 (5.5) | 7.7 (3.9) | 2.6 (1.5) | | | | |
| Composition of Ex. | 6 | 40 mg/body twice | 3.2 (1.2) | 9.8 (2.0) | 13.9 (2.9) | | 9.0 (3.8) | 13.9 (2.9) | 15.6 (2.9) | 3.8 (1.0) [3] | 7.9 (3.4) | 19.7 (4.2) | 12.5 (3.2) | 7.5 (1.2) | 1.0 (0.4) |

[2]Standard error
[3]Second administration
[4]Values on Day 4 in multiple dosing The invention will be further explained in detail by the following examples but the invention is not limited to them.

EXAMPLE 1

In a 5 liter centrifugal fluidized bed coating apparatus was placed 728.6 g of Nonpareil 103 (trade name, made by Freund Industrial Co., Ltd., main component: sugar) and 1.2 kg of a solution of 80 g of nicardipine hydrochloride, 80 g of hydroxypropyl methyl cellulose phthalate, HP-55 (trade name, made by Shin-Etsu Chemical Co., Ltd.), and 20 g of Tween-80 completely dissolved in a mixture of methanol and methyl chloride (1:1 by weight ratio) was spray-coated onto Nonpareil 103 by a conventional method to form a spherical pellet like composition. If necessary, a suitable or effective amount of talc may be added to the mixture for preventing the spherical pellet like compositions from sticking with each other. After drying the composition for 4 hours at 40° C., the composition was filled in capsules by a conventional method to provide a capsulated composition.

EXAMPLE 2

After drying the spherical pellet like composition produced as in Example 1 for 4 hours at 40° C., 90 g of an acetone-isopropanol solution of 8% Eudragit RL-100 per 500 g of the composition was spray-coated onto the composition as in Example 1 to apply a medicament permeating coating on the composition. If necessary, a small amount of talc may be added for preventing the spherical pellet like compositions from forming lumps. After drying the coated composition for 4 hours at 40° C., the composition was filled in capsules by a conventional method to provide a capsulated composition.

EXAMPLE 3

The spherical pellet like composition produced in Example 1 was blended with the spherical pellet like composition produced in Example 2 at a ratio of 3:7 by weight ratio and the resultant mixture was filled in capsules by a conventional method to provide a capsulated composition.

EXAMPLE 4

By following the same procedure as in Example 1 using 682 g. of Nonpareil 103, 1.8 kg of a methanol-methylene chloride (1:1 by weight ratio) solution having completely dissolved therein, 80 g of nicardipine hydrochloride, 80 g of Eudragit L-100 and 20 g of Tween-80, a spherical pellet like composition was obtained. If necessary, a suitable effective amount of talc may be added thereto to prevent the spherical pellet like compositions from sticking with each other. After drying the compositions for 4 hours at 40° C., the composition was filled in capsules by a conventional method to provide a capsulated composition.

EXAMPLE 5

After drying the spherical pellet like composition produced in Example 4 for 4 hours at 40° C., 200 g of an acetone-isopropanol (1:1 by weight ratio) solution having completely dissolved therein 10 g of Eudragit RL-100 was applied to 500 g of the spherical pellet like composition as in Example 1 to form a medicament permeating coating on the composition. If necessary, a proper amount of talc may be added to prevent the spherical pellet like compositions from sticking with each other. The resultant compositions was dried as in Example 4 and filled in capsules by a conventional method to provide a capsulated composition.

EXAMPLE 6

The spherical pellet like composition produced in Example 4 was blended well with the spherical pellet like composition produced in Example 5 at a ratio of 3:7 by weight ratio by a conventional method. The resultant mixture was filled in capsules by a conventional method to provide a capsulated composition.

REFERENCE EXAMPLE 1

In a fluidized bed type granulator (GLATT WSG 15) was placed 12 kg of Nonpareil 103 (24–32 mesh) and 53.3 kg of a methanol-methylene chloride (1:1 by weight ratio) solution having completely dissolved therein 4 kg of nicardipine hydrochloride and 4 kg of hydropropylmethyl cellulose (TC-5) was sprayed thereon to provide a spherical pellet like composition. The composition thus obtained was dried for 4 hours at 40° C.

EXAMPLE 7

In a fluidized bed type granulator (GLATT WSG 15) was placed 9.5 kg of Nonpareil 103 (24–32 mesh) and then 60 kg of a methanolmethylene chloride (1:1 by weight ratio) solution having completely dissolved therein 4 kg of nicardipine hydrochloride, 4 kg of Eudragit L-100, and 2 kg of Tween-80 was sprayed thereon by a conventional method to provide a spherical pellet like composition. The composition thus obtained was dried for one hour at 40° C.

Then, 18.5 kg of the spherical pellet like composition was spray-coated with 7.4 kg of a methanol-methylene chloride (1:1 by weight ratio) solution having completely dissolved therein 670 g of Eudragit RL-100 and 70 g of Macrogol 400 by a conventional method to provide a spherical pellet like composition coated with the medicament permeating material.

EXAMPLE 8

In a V-type mixer were placed 2 kg of the spherical pellet like composition produced in Reference Example 1 and 8 kg of the coated spherical pellet like composition produced in Example 7 and after adding thereto 200 g of talc, the resultant mixture was compounded until the mixture became sufficiently uniform. The mixture thus obtained was filled in capsules to provide a capsulated composition.

EXAMPLE 9

In a fluidized bed type granulator (UNIFGRATT) was placed 950 g of Nonpareil 103 (less than 32 mesh) and then a 20% water-containing methanol solution having dispersed and dissolved therein 400 g of nicardipine hydrochloride 400 g of Eudragit L-100, and 100 g of Tween 80 was sprayed thereon by a conventional method to provide a spherical pellet like composition. The composition thus obtained was dried for about 4 hours at 40° C. Then, 1,850 g of the spherical pellet like composition was spray-coated with 740 g of a methanol-methylene chloride (1:1 by weight ratio) solution having dissolved therein 50 g of Ethocell CP-10, 50 g of hydroxypropylmethyl cellulose (TC-5), and 11 g of Macrogol 400, by a conventional method to apply a medicament permating coating.

Then, 800 g of the coated spherical pellet like composition thus produced was unformly mixed with 200 g of the spherical pellet like composition produced in Reference Example 1 by the same manner as in Example 8 and the resultant mixture was filled in capsules to provide a capsulated composition.

REFERENCE EXAMPLE 2

By spray-coating 200 g of Nonpareil 103 (32–42 mesh) with 1.8 kg of a methanol-methylene chloride (1:1 by weight ratio) solution having completely dissolved therein 80 g of nicardipine hydrochloride, 80 g of Eudragit L-100, and 40 g of Macrogoal 1500 by a conventional method, a spherical pellet like composition was obtained.

What is claimed is:

1. A spherical pellet-like nicardipine long acting composition comprising a pharmaceutically inert core coated with the following components:
   (a) a pharmaceutically active amount of amorphous nicardipine or a hydrochloride salt thereof,
   (b) a pH-dependent additive selected from the group consisting of hydroxypropylmethyl cellulose phthalate, cellulose acetate phthalate, poly(methacrylic acid, methylmethacrylate) and shellac,
   (c) a surface active agent selected from the group consisting of polyoxyethylene sorbitan fatty acid ester, polyoxyethylene alkyl ether and polyoxyethylene hydrogenated castor oil, and further coated with
   (d) at least one medicament penetrating material selected from the group consisting of poly(ethylacrylate, methylmethacrylate, trimethylammonioethylmethacrylate chloride) and ethyl cellulose;
   wherein the ratio of components (a), (b) and (c) to said inert core is 1:01 to 1:10, and wherein said composition is comprised of from 99 to 85 parts of said inert core plus components (a), (b) and (c), and from 1 to 15 parts of component (d).

2. The long acting composition of claim 1 wherein said core is coated with amorphous nicardipine.

3. The long acting composition of claim 1 wherein said core is coated with amorphous nicardipine hydrochloride.

4. The long acting composition of claim 1 wherein said pH-dependent additive is hydroxypropylmethyl cellulose phthalate.

5. The long acting composition of claim 1 wherein said pH-dependent additive is cellulose acetate phthalate.

6. The long acting composition of claim 1 wherein said pH-dependent additive is poly(methacrylic acid, methylmethacrylate).

7. The long acting composition of claim 1 wherein said pH-dependent additive is shellac.

8. The long acting composition of claim 1 wherein said surface active agent is polyoxyethylene sorbitan fatty acid ester.

9. The long acting composition of claim 1 wherein said surface active agent is polyoxyethylene alkyl ether.

10. The long acting composition of claim 1 wherein said surface active agent is polyoxyethylene hydrogenated castor oil.

11. The long acting composition of claim 1 wherein said medicament penetrating material is poly(ethylacrylate methylmethacrylate trimethylammonioethylmethacrylate chloride).

12. The long acting composition of claim 1 wherein said medicament penetrating material is ethyl cellulose.

13. A spherical pellet-like nicardipine long acting composition comprising a pharmaceutically inert core coated with the following components:
   (a) a pharmaceutically active amount of amorphous nicardipine hydrochloride,
   (b) a pH-dependent additive consisting of hydroxypropylmethyl cellulose phthalate,
   (c) a surface active agent consisting of polyoxyethylene sorbitan fatty acid ester, and further coated with
   (d) a medicament penetrating material consisting of poly(ethylacrylate, methylmethacrylate, and trimethylammonioethylmethacrylate chloride);
   wherein the ratio of components (a), (b) and (c) to said inert core is 1:01 to 1:10, and wherein said composition is comprised of from 99 to 85 parts of said inert core plus components (a), (b) and (c), and from 1 to 15 parts of component (d).

* * * * *

UNITED STATES PATENT AND TRADEMARK OFFICE
CERTIFICATE OF CORRECTION

PATENT NO. : 4,758,437

DATED : July 19, 1988

INVENTOR(S) : Takashi Sonobe, et al

It is certified that error appears in the above-identified patent and that said Letters Patent is hereby corrected as shown below:

Column 8

Claim 13, line 12: delete "and".

Signed and Sealed this

Seventh Day of February, 1989

Attest:

DONALD J. QUIGG

Attesting Officer

Commissioner of Patents and Trademarks